US010928038B2

(12) United States Patent
Shibata et al.

(10) Patent No.: US 10,928,038 B2
(45) Date of Patent: Feb. 23, 2021

(54) LIGHT SOURCE DEVICE COMPRISING WAVELENGTH CONVERTING MEMBER WITH FIRST CONVERTING MATERIAL AND SECOND CONVERTING MATERIAL THAT EMITS LIGHT HAVING A WAVELENGTH LONGER THAN THE FIRST WITH AN AFTER GLOW TIME OF THE SECOND LONGER THAN AN EMISSION

(71) Applicant: PANASONIC INTELLECTUAL PROPERTY MANAGEMENT CO., LTD., Osaka (JP)

(72) Inventors: Yudai Shibata, Hyogo (JP); Shintaro Hayashi, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/822,504

(22) Filed: Mar. 18, 2020

(65) Prior Publication Data

US 2020/0309348 A1 Oct. 1, 2020

(30) Foreign Application Priority Data

Mar. 28, 2019 (JP) .............................. JP2019-063402

(51) Int. Cl.
*F21V 9/32* (2018.01)
*F21V 7/04* (2006.01)
(52) U.S. Cl.
CPC ................ *F21V 9/32* (2018.02); *F21V 7/043* (2013.01)

(58) Field of Classification Search
CPC ..................................... F21V 9/32; F21V 9/38
See application file for complete search history.

(56) References Cited

U.S. PATENT DOCUMENTS

| 2017/0188803 | A1 | 7/2017 | Yabe et al. | |
| 2018/0274753 | A1* | 9/2018 | Sakaino | .................. B32B 27/36 |
| 2020/0010760 | A1* | 1/2020 | Ueda | ....................... H01L 33/50 |

FOREIGN PATENT DOCUMENTS

| JP | 2006-117857 A | 5/2006 |
| JP | 5543760 B2 | 7/2014 |
| JP | 6059406 B2 | 1/2017 |

* cited by examiner

*Primary Examiner* — Robert J May
(74) *Attorney, Agent, or Firm* — Greenblum & Bernstein, P.L.C.

(57) ABSTRACT

A wavelength converting member includes a first wavelength converting material and a second wavelength converting material. The emission wavelength of the second wavelength converting material is longer than the emission wavelength of the first wavelength converting material, and in the second wavelength converting material, the time from when excitation light stops to when fluorescence stops is an afterglow time, and the afterglow time is longer than the emission time of the first wavelength converting material and is 1 s or less. A light source device includes the wavelength converting member and a light source unit. A lighting device includes the wavelength converting member, a light source device, and a light guide disposed between the light source unit and the wavelength converting member.

5 Claims, 4 Drawing Sheets

LIGHT SOURCE DEVICE COMPRISING WAVELENGTH CONVERTING MEMBER WITH FIRST CONVERTING MATERIAL AND SECOND CONVERTING MATERIAL THAT EMITS LIGHT HAVING A WAVELENGTH LONGER THAN THE FIRST WITH AN AFTER GLOW TIME OF THE SECOND LONGER THAN AN EMISSION

CROSS REFERENCE TO RELATED APPLICATION

The entire disclosure of Japanese Patent Application No. 2019-063402 filed on Mar. 28, 2019 including the specification, claims, drawings, and abstract is incorporated herein by reference in its entirety.

TECHNICAL FIELD

Background

The present disclosure relates to a wavelength converting member, a light source device, and a lighting device.

In recent years, in medical imaging devices such as endoscopes, an observation method for special light observation, which uses special light, has been devised in addition to normal observation, which uses white light. For instance, in photodynamic diagnosis (PDD), when an indocyanine green (ICG) aqueous solution is injected into a blood vessel and the energy state of ICG is increased by irradiation with near-infrared light, the solution emits near-infrared fluorescence with a wavelength slightly longer than that of the radiated near-infrared light, which can be used to observe the state of lymph glands and the like. Here, observation with white light and observation with near-infrared light are performed.

In order to output light having different wavelengths such as white light and near-infrared light, multiple light sources are required, and conventionally, a combination of a discharge lamp and a color filter and the like has been used. In recent years, there have been developments relating to light source devices and lighting devices, as light sources, in which a wavelength converting member that converts light output from solid-state light emitting elements, such as LEDs and laser diodes, into red, green, and blue light are used to obtain the three primary colors of light, and outputs them as light having desired color rendering properties utilizing time-sharing technology.

JP 2006-117857 A relates to a light source device that can be used for an endoscope. Here, as conventional technology, a color projector is described in which a solid light emitting element that outputs violet or ultraviolet light is used as a pump source, three phosphors that convert excitation light into red, green, and blue fluorescence are used, and the solid light emitting element is driven in a time-sharing manner in order to output fluorescence of colors corresponding to image data. In this case, the light emission times of the three phosphors differ depending on the image data, so that the temperature rises of the three phosphors differ and the light emission efficiency changes.

The prior art, which provides each of the three phosphors to a rotating body and adjusts the rotation speed of the rotating body to equalize the temperature rise, requires a solid light emitting element and a rotating body for each of the three phosphors. Therefore, in JP 2006-117857 A, red, green, blue, and amber phosphors are disposed in each of four annular bands separated from each other in the radial direction of the rotating body, so that the rotating bodies can be combined into one.

JP 6059406 B describes a light source device that combines multiple laser lights into light having a wavelength suitable for specimen observation in a microscope system that irradiates a specimen with laser light so that the specimen can be observed with a microscope. Here, a notch filter is used as a wavelength selection optical element that reflects only the laser light having a wavelength emitted from the laser light source and transmits light having other wavelengths. For example, three laser light sources having different wavelengths and three notch filters are combined to align the reflection optical axes of the respective notch filters so that light enters a small aperture of the fiber core of the optical fiber, thereby combining laser light of three wavelengths.

Regarding a technique related to the present disclosure, JP 5543760 B describes a technique for extending the afterglow time of a luminous material. Here, two luminous materials are used, and once they are irradiated with excitation light, the two luminous materials each generate afterglow for a certain period of time even after the irradiation with the excitation light is stopped. It is also mentioned that even after the irradiation with excitation light is stopped, the afterglow of the luminous material on one side irradiates the luminous material on the other side, so that the duration of the afterglow of the luminous material on the other side is extended. It is mentioned that the irradiation time of the excitation light varies depending on the type of the light source, the irradiation intensity, and the distance from the light source, and is, for example, about 10 minutes to one hour.

SUMMARY

Technical Problem

In medical imaging devices, such as endoscopes, noise between white light and special light is preferably reduced in order to image an object using white light and special light for appropriate observation. Time-division emission is used as a method for reducing noise between lights of multiple wavelengths, and, as a prior art technique, includes a method using a rotating body with a phosphor and a driving device for the rotating body, and a method using multiple light sources and multiple optical mirrors to accurately align optical axes, which are both complex and high in cost.

There is therefore a demand for a wavelength converting member that can suppress noise between lights of multiple wavelengths with an inexpensive and highly reliable configuration, a light source device that uses the wavelength converting member, and a lighting device that uses the wavelength converting member.

Solution To Problem

A wavelength converting member according to the present disclosure includes: a first wavelength converting material; and a second wavelength converting material. The emission wavelength of the second wavelength converting material is longer than the emission wavelength of the first wavelength converting material, and in the second wavelength converting material, the time from when excitation light stops to when fluorescence stops is an afterglow time, and the afterglow time is longer than the emission time of the first wavelength converting material and is 1 s or less.

A light source device according to the present disclosure includes the wavelength converting member and a light source unit. A lighting device according to the present disclosure includes the wavelength converting member, a light source unit, and a light guide disposed between the wavelength converting member and the light source.

ADVANTAGEOUS EFFECTS OF INVENTION

According to the wavelength converting member, the light source device, and the lighting device with such a configuration, noise between lights having multiple wavelengths can be suppressed with an inexpensive and highly reliable configuration.

BRIEF DESCRIPTION OF DRAWINGS

The figures depict one or more implementations in accordance with the present teaching, by way of example only, not by way of limitations. In the figures, like reference numerals refer to the same or similar elements.

An embodiment of the present disclosure will be described based on the following figures, wherein.

DESCRIPTION OF EMBODIMENTS

An embodiment of the present disclosure will now be described in detail with reference to the accompanying drawings. The wavelengths and the like described below are merely illustrative for description and can be changed as appropriate depending on the specifications of the wavelength converting member, light source device, and lighting device. Regarding the description below, the same components are denoted by the same reference numerals in all the drawings, and overlapping description will be omitted.

Figure 1:
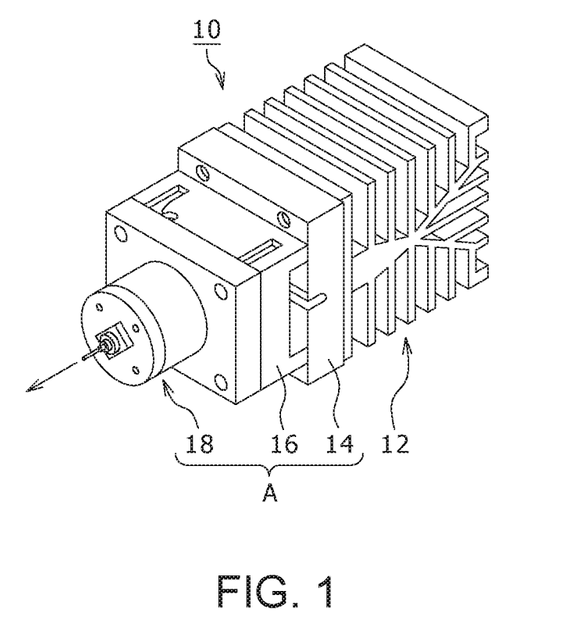
FIG. 1 is a perspective view of a lighting device including a wavelength converting member according to an embodiment.

FIG. 1 is a perspective view of a lighting device 10 including a wavelength converting member. When applied to an endoscope system 50 (see FIG. 5), the lighting device 10 is a device for illuminating an observation target with light. The lighting device 10 includes a fin unit 12 for heat dissipation, a light source unit 14 in which a pump source is disposed, a wavelength converting unit 16 in which wavelength converting members that output multiple types of light having different wavelengths upon excitation are disposed, and an optical fiber connecting unit 18 including the connection port to an optical fiber 56 (see FIG. 5) in the endoscope system 50.

Figure 2:
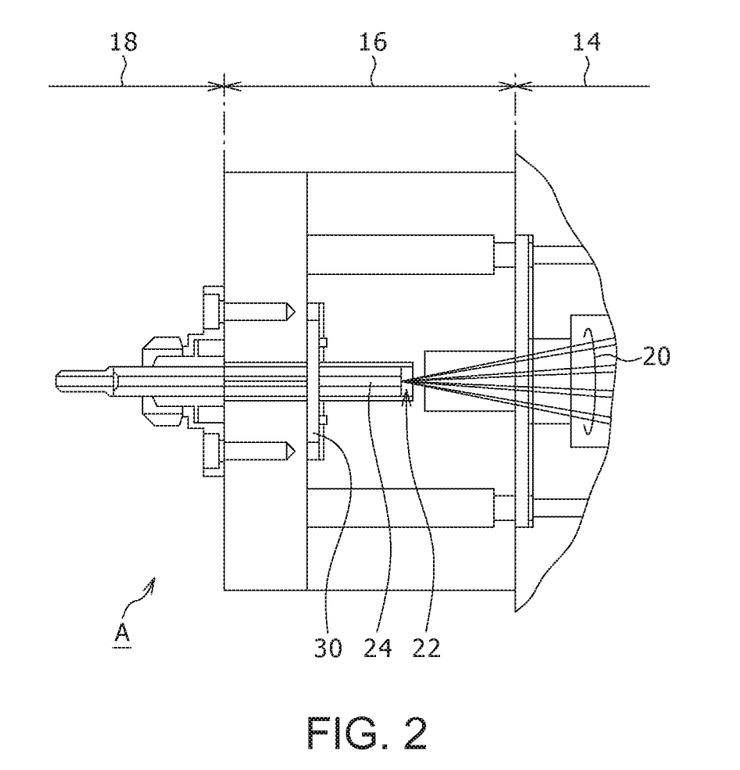
FIG. 2 is a cross-sectional view of the part A in FIG. 1.

FIG. 2 is a cross-sectional view of a portion A including a portion of the light source unit 14, the wavelength converting unit 16, and the optical fiber connecting unit 18 shown in FIG. 1.

Figure 5:
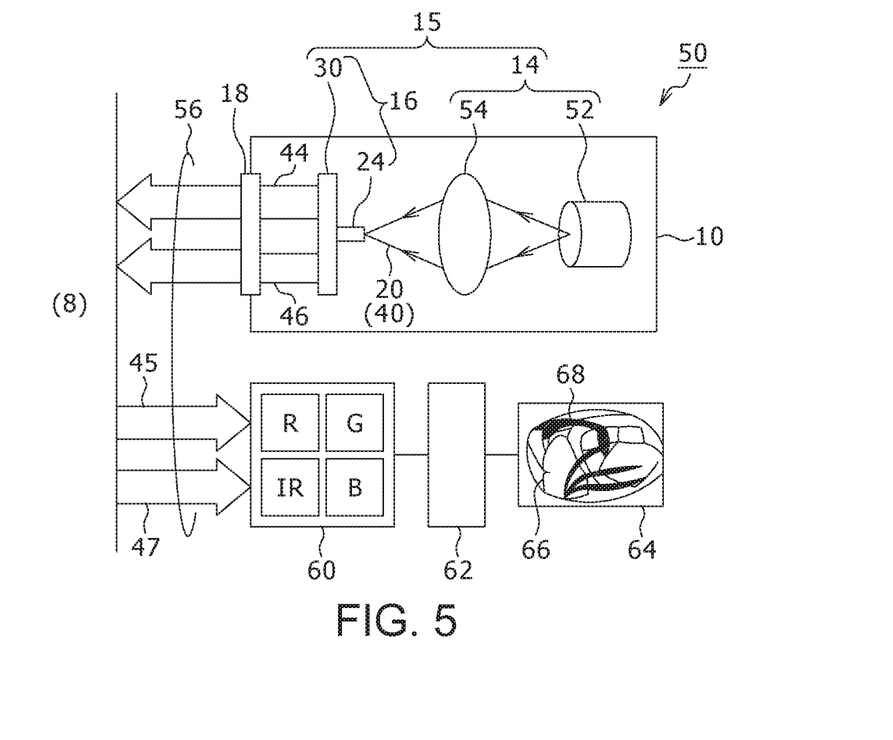
FIG. 5 is a configuration diagram showing the case where a lighting device including the wavelength converting member according to the embodiment is applied to an endoscope system.

The light source unit 14 includes a laser light source 52 as a pump source and a condenser lens system 54 (see FIG. 5). A blue laser is used as the laser light source 52. This is merely illustrative for explanation, and the pump source of the light source unit 14 may be any light source that can excite the phosphor. Alternatively, a laser light source 52 other than the blue laser or an LED light source may be used depending on the specifications of the lighting device 10 and the endoscope system 50. The condenser lens system 54 is an optical element that focuses the laser beam emitted from a laser light source 52 and condenses it at a predetermined focal position 22. The laser light 20 focused by the condenser lens system 54 is incident on the wavelength converting unit 16.

The wavelength converting unit 16 is a member that wraps the wavelength converting member 30. The wavelength converting member 30 is disposed adjacent to the optical fiber connecting unit 18 in the wavelength converting unit 16. The focal position 22 of incident laser light 20 that is focused by the condenser lens system 54 in the light source unit 14 is adjacent to the light source unit 14 in the wavelength converting unit 16. The light guide 24 is a light guide member that guides the laser light 20 from the focal position 22 of the laser light 20 adjacent to the light source unit 14 to the wavelength converting member 30 while making the laser light 20 uniform. For example, a cylindrical body in which four mirrors called mirror rods are bonded can be used as the light guide 24. The light guide 24 is preferably provided between the wavelength converting member 30 and the optical fiber connecting unit 18.

Figure 3:
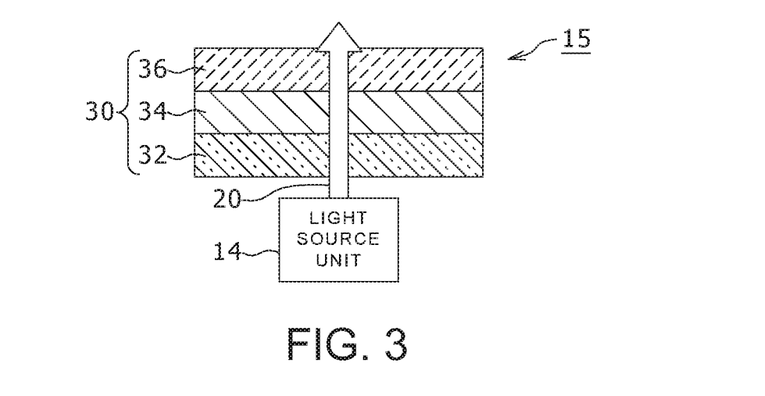
FIG. 3 is a diagram showing the components of the light source device of the embodiment, extracted from the lighting device of FIG. 1.

FIG. 3 is a diagram showing an extracted configuration of the light source device 15, omitting the light guide 24 and the optical fiber connecting unit 18 from the lighting device 10. The light source device 15 includes a light source unit 14 and a wavelength converting member 30.

The wavelength converting member 30 is an optical element that converts the laser light 20 having a single wavelength into multiple types of light having different wavelengths, and outputs the multiple types of light obtained by conversion. Here, in order to obtain light having two different wavelengths by conversion, a first wavelength converting material 34 and a second wavelength converting material 36 are laminated on the transparent substrate 32, thereby forming the wavelength converting member 30 having a single plate.

The transparent substrate 32 is an optical substrate on which a laminate of the first wavelength converting material 34 and the second wavelength converting material 36 is supported, and transmits the laser light 20. A sapphire substrate is used as the transparent substrate 32. In some cases, a glass substrate can be used.

The first wavelength converting material 34 is disposed adjacent to the transparent substrate 32, and is the first component that receives the laser light 20 incident on the transparent substrate 32. The second wavelength converting material 36 is stacked on the first wavelength converting material 34, and receives the laser light 20 that has passed through the first wavelength converting material 34.

The first wavelength converting material 34 and the second wavelength converting material 36 each contain a fluorescent material that is excited by the laser light 20 and the contained fluorescent materials are different, and they have the following relationship depending on the difference in the contained fluorescent materials. In other words, the emission wavelength of the second wavelength converting material 36 is longer than the emission wavelength of the first wavelength converting material 34, and the emission time of the second wavelength converting material 36 is longer than the emission time of the first wavelength converting material 34.

The first wavelength converting material 34 contains a fluorescent material that emits fluorescence having the wavelength of yellow that is complementary to blue. The pyramidal cells that recognize the color in the human eye recognize white light when they sense light with a yellow wavelength, so the fluorescent material that emits fluorescence with a yellow wavelength emits pseudo white fluorescence. Accordingly, white fluorescence will hereinafter be referred to as white light 44 unless otherwise specified. A YAG: Ce-based phosphor that is excited by light having a blue wavelength of about 450 nm and emits yellow light having a wavelength of about 550 nm can be used as the first wavelength converting material 34. This is merely illustrative for description, and any phosphor that is excited by light emitted from the light source unit 14 and emits white light 44 may be used.

The second wavelength converting material 36 contains a fluorescent material that emits fluorescence having a near-infrared wavelength, and the emission duration time of the fluorescence after the irradiation with the laser light 20 is stopped is longer than the emission duration time of the first wavelength converting material 34. A GSG (Ga, Sc, Ga) -based phosphor having the composition expressed by Formula (1) is used as the second wavelength converting material 36.

[Formula 1]

$$(Gd_{1-x}La_x)_3(Ga_{1-y-z}Sc_yCr_z)_2Ga_3O_{12} \quad (1)$$

Here, x, y, and z are preferably in the range expressed by Formula (2).

[Formula 2]

$$0.1 \leq x \leq 0.6$$

$$0.4 \leq y \leq 0.8$$

$$0.001 \leq z \leq 0.1 \quad (2)$$

The second wavelength converting material 36 having the composition expressed by Formula (1) emits near-infrared fluorescence having a wavelength of about 770 nm to about 820 nm as the peak wavelength $\lambda p$ upon selection of the parameter expressed by Formula (2). Hereinafter, near-infrared fluorescence will be referred to as near-infrared light 46 unless otherwise specified. With the second wavelength converting material 36, the emission duration time of the near-infrared light 46 after the irradiation with the laser light 20 is stopped is sufficiently longer than the emission duration time of the white light 44 of a YAG: Ce-based phosphor that is the first wavelength converting material 34.

Figure 4:
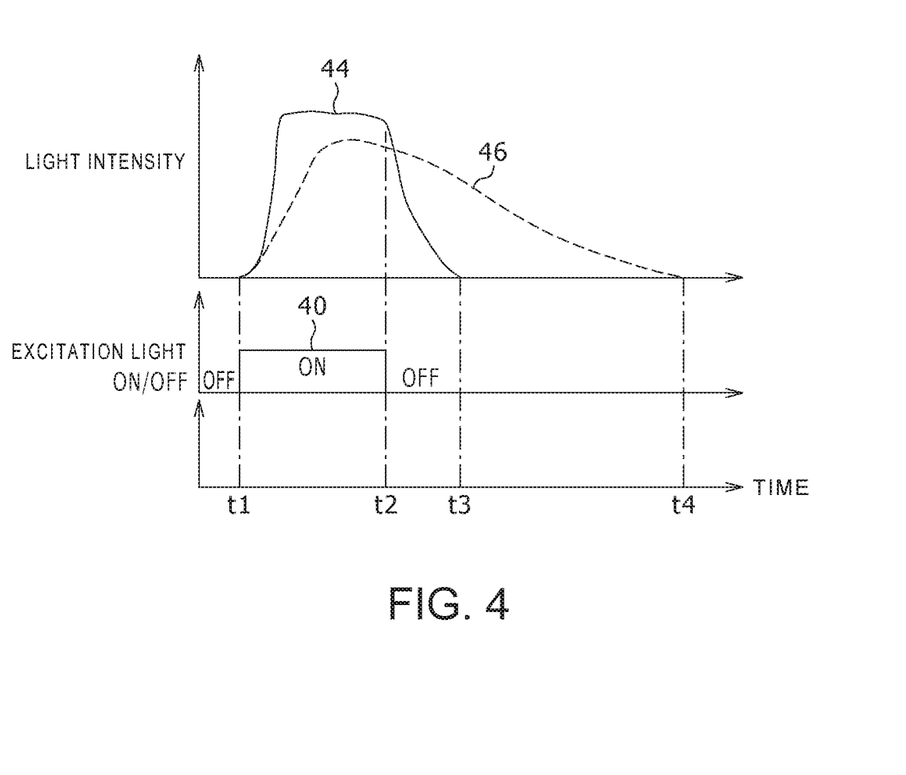
FIG. 4 is a diagram showing the relationship between the emission times of white light and near-infrared light observed when the wavelength converting member is pumped in the light source device shown in FIG. 3.

When the light source unit 14 is intermittently lit in the light source device 15, the laser light 20 is emitted during the lit period to excite the wavelength converting member 30. FIG. 4 shows the relationship between the emission time of the white light 44 emitted from the first wavelength converting material 34 and the emission time of the near-infrared light 46 emitted from the second wavelength converting material 36 observed when the first wavelength converting material 34 and the second wavelength converting material 36 are excited by the laser light 20. In FIG. 4, the horizontal axis represents time, and the vertical axis represents the ON/OFF state of the excitation light 40 and the light intensities of the white light 44 and the near-infrared light 46. Regarding ON/OFF of the excitation light 40, ON refers to the lit state, and OFF refers to the light-off state in the case where the laser light source 52 in the light source unit 14 is intermittently lit. The unit of light intensity is arbitrary.

In FIG. 4, time t1 is the time for the excitation light 40 to switch from the OFF state to the ON state, and time t2 is the time for the excitation light 40 to switch from the ON state to the OFF state. The period from time t1 to time t2 is a period in which the first wavelength converting material 34 and the second wavelength converting material 36 are excited by the laser light 20.

When emission of white light 44 is started from time t1 and the light intensity of the white light 44 rapidly increases and reaches a peak, the first wavelength converting material 34 keeps the peak of the intensity of the white light 44 until time t2 at which irradiation with the excitation light 40 stops. After the time t2, the light intensity of the white light 44 decreases with time, and substantially no light is emitted at time t3. The emission time of the white light 44 is the period from the time t1 to the time t3.

The second wavelength converting material 36 starts to emit the near-infrared light 46 at the time t1, and the light intensity of the near-infrared light 46 increases with time, but the rise of the light intensity of the near-infrared light 46 is gradual compared to the rise of the light intensity of the white light 44. The light intensity of the near-infrared light 46 reaches a peak around the time t2 at which the irradiation with the excitation light 40 stops. Accordingly, since the irradiation with the excitation light 40 stops around the peak, even after reaching the peak, the near-infrared light 46 is not maintained at the peak, so that the light intensity of the near-infrared light 46 decreases with time. The decrease in the light intensity of the near-infrared light 46 is much more gradual than the decrease in the light intensity of the white light 44, and substantially no light is emitted at the time t4 that is much later than the time t3. The emission time of the near-infrared light 46 is the period from the time t1 to the time t4.

The overall wavelength converting member 30 in which the first wavelength converting material 34 and the second wavelength converting material 36 are laminated is in the emission state in which the white light 44 and the near-infrared light 46 are mixed. As shown in FIG. 4, the overall wavelength converting member 30 is in the emission state in which, during the period from the time t1 to the time t2, the light intensity of the white light 44 is higher than the light intensity of the near-infrared light 46 and the white light state is dominant to human eyes. In contrast, since the light intensity of the near-infrared light 46 becomes higher than the light intensity of the white light 44 immediately after the time t2, the near-infrared light state becomes dominant. In other words, during the period in which the near-infrared light 46 is dominant, there is a state in which the light intensity of the white light 44 is negligible with respect to the light intensity of the near-infrared light 46, and noise between the near-infrared light 46 and the white light 44 is suppressed. In order to make the light intensity of the white light 44 negligible with respect to the light intensity of the near-infrared light 46, depending on the specifications of the S/N ratio of the near-infrared light 46 to the white light 44, for example, the light intensity of the white light 44 is 50% or less, preferably 10% or less, with respect to the light intensity of the near-infrared light 46.

In the above description, the phosphor contained in the second wavelength converting material 36 is excited by the laser light 20 and emits the near-infrared light 46. Alternatively, as shown in FIG. 4, during the period from the time t1 to the time t3, the phosphor of the first wavelength converting material 34 is irradiated with the white light 44 emitted by the phosphor. The phosphor of the second wavelength converting material 36 is also excited by this irradiation with the white light 44. Under the influence of the excitation by the white light 44, the emission efficiency of the near-infrared light 46 is slightly lowered, while the emission time is longer than upon excitation by the laser light 20 alone.

In the above description, the wavelength converting member 30 has a configuration in which the transparent substrate 32, the first wavelength converting material 34, and the second wavelength converting material 36 are laminated in this order from the side on which the laser light 20 is incident. This order of lamination provides a structure in which the near-infrared light 46 emitted from the second wavelength converting material 36 is not absorbed by the first wavelength converting material 34. When the transparent substrate 32, the second wavelength converting material 36, and the first wavelength converting material 34 are laminated in this order from the side on which the laser light 20 is incident, the near-infrared light 46 emitted from the second wavelength converting material 36 is absorbed when passing through the first wavelength converting material 34, so that the emission efficiency of the near-infrared light 46 decreases.

Both the emission time of the white light 44 (t3–t1) and the emission time of the near-infrared light 46 (t4–t1) are set to about one frame period $T_F$ of image data in the endoscope system 50. Although one frame period $T_F$ of image data in an imaging system such as a high-speed camera is, for example, (1/60) s, in the endoscope system 50, it may be (1/30) s or (1/15) s depending on the specifications. If the time from when the excitation light stops until when the fluorescence stops is the afterglow time, the afterglow time of the fluorescent material contained in the first wavelength converting material 34 and the afterglow time of the fluorescent material contained in the second wavelength converting material 36 is 1 s or less at most, which is overwhelmingly shorter than the emission time or afterglow time of the luminous material, which is several hours.

In the above description, the wavelength converting member 30 is a plate member in which the first wavelength converting material 34 and the second wavelength converting material 36 are laminated. Alternatively, a mixture of a first phosphor that emits white light 44 upon excitation by the laser light 20 and a second phosphor that emits near-infrared light 46 may be molded into a plate shape to be the wavelength converting member 30. The wavelength converting member 30 in the form of a laminate is improved from that in the form of a mixture in terms of the assembly accuracy of the light source device 15 and the lighting device 10. However, in terms of the cost, use of the mixture is advantageous compared with use of the laminate.

FIG. 5 is a configuration diagram of the endoscope system 50 including the lighting device 10 using the wavelength converting unit 16. In the endoscope system 50, the white light 44 and the near-infrared light 46 emitted from the lighting device 10 are shone on an object 8 through the optical fiber 56. In this system, light that is dependent on the shape or the like of the irradiated object 8 is returned to the imaging device 60 via the optical fiber 56 and shown on the display 64 via the image converting unit 62.

The lighting device 10 includes a laser light source 52 and a condenser lens system 54 as the light source unit 14. Under the control by a control unit (not shown), the laser light source 52 blinks every predetermined frame period $T_F$, and emits the blue laser light 20 as the excitation light 40 in the lit period. The lit period is the ON period of the excitation light 40 in FIG. 4 (from the time t1 to the time t2). The laser light 20 is focused by the condenser lens system 54 and enters the wavelength converting member 30 via the light guide 24 of the wavelength converting unit 16. As described with reference to FIG. 3, a portion in which the light guide 24 is omitted and the light source unit 14 and the wavelength converting member 30 are included is the light source device 15. The white light 44 and the near-infrared light 46 are emitted from the wavelength converting unit 16 in the emission relationship described with reference to FIG. 4, and are shone on the object 8. The object 8 is a living body.

The white light 45 and the near-infrared light 47 corresponding to the emitted white light 44 and near-infrared light 46 are guided from the irradiated object 8 to the optical fiber 56.

The imaging device 60 includes four types of imaging elements represented by R, G, B, and IR in FIG. 5. The imaging element represented by R detects red light, the imaging element represented by G detects green light, the imaging element represented by B detects blue light, and the imaging element represented by IR detects near-infrared light. The intensities of four types of light detected by the four types of imaging elements are transmitted to the image converting unit 62, undergo appropriate image signal processing, are transmitted to the display 64 as image data indicating the shape or the like of the object 8, and are displayed as an image. Image data is transmitted every frame period $T_F$.

The image converting unit 62 can transmit the shape or the like detected by the imaging element represented by IR to the display 64 as image data with special coloring. For example, when an indocyanine green (ICG) aqueous solution is injected into a blood vessel of a living body, which is the object 8, and irradiated with the near-infrared light 46, the energy state of the ICG increases and near-infrared light 47 with a wavelength slightly longer than that of the radiated near-infrared light 46 is emitted. This can be used to observe the state of the lymph glands and the like. On the display 64 shown in FIG. 5, regarding the living body which is the object 8, the shaped parts of lymph glands based on the near-infrared light 47 are represented by the colored portion 68 together with the shape 66 of internal organs and the like based on the white light 45.

Figure 6:
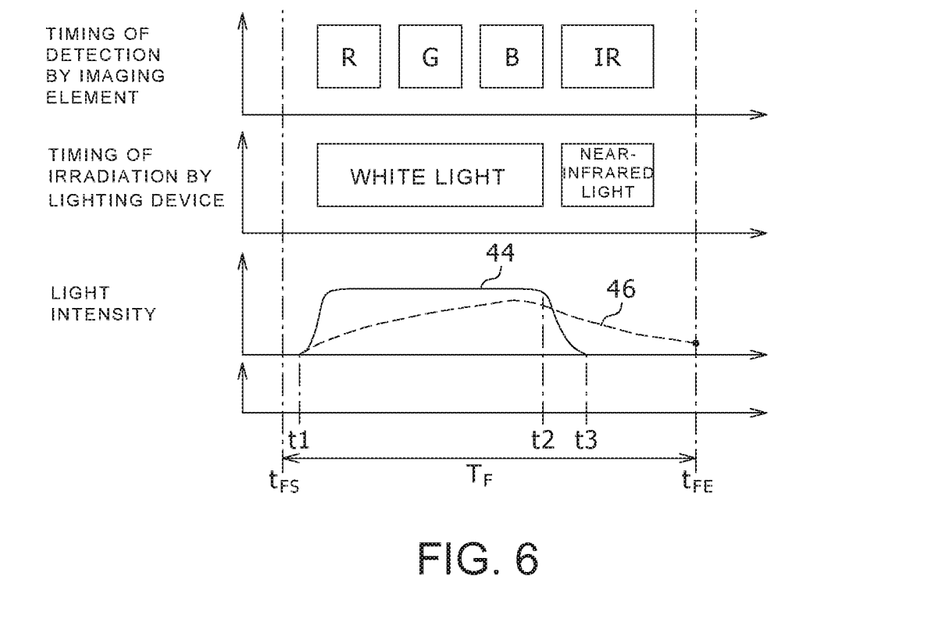
FIG. 6 is a diagram showing the relationship between the emission sequence of the illumination light of the lighting device and the imaging sequence of the imaging device on the same time axis in the configuration shown in FIG. 5.

FIG. 6 is a diagram showing the relationship between the timing of detection by each of the four types of imaging elements in the imaging device 60 and the timing of irradiation by the lighting device 10 in the endoscope system 50. In FIG. 6, the horizontal axis represents time, and the time axis represents the frame period $T_F$. The vertical axis represents, from the top to the bottom of the drawing, the timing of detection by the imaging element, the timing of irradiation by the lighting device 10, and the light intensities of the white light 44 and the near-infrared light 46 emitted from the wavelength converting unit 16. The characteristic chart at the bottom is the same as in FIG. 4.

In the imaging device 60 during the frame period $T_F$, of the four types of imaging elements, the imaging element represented by R, the imaging element represented by G, the imaging element represented by B, and then the imaging element represented by IR operate in this order, and red light, green light, blue light, and then near-infrared light are detected in this order in time sequence. Correspondingly, the lighting device 10 emits the white light 44 over the operation period of the imaging element represented by R, the operation period of the imaging element represented by G, and the operation period of the imaging element represented by B in the imaging device 60. Further, the lighting device 10 emits near-infrared light 46 over the operation period of the imaging element represented by IR in the imaging device 60.

In the prior art, a complex configuration for time-division irradiation is used such that irradiation with near-infrared light 46 is performed after irradiation with white light 44. In contrast, in the lighting device 10, the wavelength converting unit 16 including the first wavelength converting material 34 that emits white light 44 and the second wavelength converting material 36 that emits near-infrared light 46 is used so that excitation light 40 is supplied from one laser light source 52 to the wavelength converting unit 16. Here, in order to make the emission time of the near-infrared light 46 emitted from the second wavelength converting material 36 longer than the emission time of the white light 44 emitted from the first wavelength converting material 34, the phosphor in the composition represented by (1) is used in the second wavelength converting material 36. This leaves a period in which the white light 44 is dominant and a period in which the near-infrared light 46 is dominant. In the lighting device 10, the period from the time t1 to the time t2 in which the white light 44 is dominant is assigned to the period over the operation period of the imaging element represented by R, the operation period of the imaging element represented by G, and the operation period of the imaging element represented by B in the imaging device 60. Consequently, the period from immediately after the time t2 to the end time $t_{FE}$ of the frame period $T_F$ becomes a period in which the near-infrared light 46 is dominant. The imaging element represented by IR in the imaging device 60 operates in a period in which the near-infrared light 46 is dominant.

According to the above configuration, the emission time as a material characteristic of the phosphor is controlled by using phosphor having an appropriate composition, thereby leaving a period in which the white light 44 is dominant and a period in which the near-infrared light 46 is dominant.

Hence, in the wavelength converting member 30, the light source device 15, and the lighting device 10 having the above-described configuration, noise between lights of multiple wavelengths can be suppressed with an inexpensive and highly reliable configuration.

The invention claimed is:

1. A light source device, comprising:
   a wavelength converting member; and
   a light source unit, wherein
   the wavelength converting member comprises:
   a first wavelength converting material; and
   a second wavelength converting material, wherein
      an emission wavelength of the second wavelength converting material is longer than an emission wavelength of the first wavelength converting material, and
      in the second wavelength converting material, the time from when excitation light stops to when fluorescence stops is an afterglow time, and the afterglow time is longer than the emission time of the first wavelength converting material and is 1 s or less, wherein,
   when the light source unit is intermittently lit, there is a state where a light intensity of the emission by the first wavelength converting material is 50% or less of the light intensity of the emission by the second wavelength converting material.

2. The light source device according to claim 1, wherein the first wavelength converting material and the second wavelength converting material are in a laminated structure.

3. The light source device according to claim 1, wherein the first wavelength converting material and the second wavelength converting material are in a mixture.

4. The light source device according to claim 1, wherein the second wavelength converting material is also excited by emission by the first wavelength converting material.

5. A lighting device comprising:
   the light source device according to claim 1; and
   a light guide provided between the wavelength converting member and the light source unit.

* * * * *

UNITED STATES PATENT AND TRADEMARK OFFICE
CERTIFICATE OF CORRECTION

| | |
|---|---|
| PATENT NO. | : 10,928,038 B2 |
| APPLICATION NO. | : 16/822504 |
| DATED | : February 23, 2021 |
| INVENTOR(S) | : Yudai Shibata et al. |

It is certified that error appears in the above-identified patent and that said Letters Patent is hereby corrected as shown below:

On the Title Page

Item (54), please add -- TIME OF THE FIRST -- to the end of the title.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*